(12) United States Patent
Yahiro et al.

(10) Patent No.: US 8,963,917 B2
(45) Date of Patent: Feb. 24, 2015

(54) RADIOLOGICAL BREAST IMAGE DISPLAY METHOD, RADIOLOGICAL BREAST IMAGE DISPLAY APPARATUS, AND PROGRAM

(71) Applicant: FUJIFILM Corporation, Tokyo (JP)

(72) Inventors: Yasuko Yahiro, Ashigarakami-gun (JP); Takao Kuwabara, Ashigarakami-gun (JP); Yasunori Ohta, Ashigarakami-gun (JP); Akira Hasegawa, San Jose, CA (US)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 14/039,618

(22) Filed: Sep. 27, 2013

(65) Prior Publication Data

US 2014/0022247 A1    Jan. 23, 2014

Related U.S. Application Data

(63) Continuation of application No. PCT/JP2012/002168, filed on Mar. 29, 2012.

(60) Provisional application No. 61/470,041, filed on Mar. 31, 2011.

(51) Int. Cl.
*G06T 15/00*    (2011.01)
*G06K 9/00*    (2006.01)
(Continued)

(52) U.S. Cl.
CPC ............... *G06T 15/005* (2013.01); *A61B 6/022* (2013.01); *A61B 6/502* (2013.01);
(Continued)

(58) Field of Classification Search
CPC ............... A61B 6/022; H04N 13/0221; H04N 13/0003; H04N 13/0296; H04N 13/0402; H04N 13/0438; H04N 13/0239; Y10S 128/916
See application file for complete search history.

(56) References Cited

U.S. PATENT DOCUMENTS 6,181,768 B1 *    1/2001    Berliner ........................ 378/41
6,272,233 B1 *    8/2001    Takeo ........................... 382/128
(Continued)

FOREIGN PATENT DOCUMENTS

EP    2 371 287 A1    10/2011
JP    2007-195663 A    8/2007
(Continued)

OTHER PUBLICATIONS

International Search Report, mailed Aug. 14, 2012, issued in PCT/JP2012/002168.
(Continued)

*Primary Examiner* — Joni Richer
*Assistant Examiner* — Yi Wang
(74) *Attorney, Agent, or Firm* — Birch, Stewart, Kolasch & Birch, LLP

(57) ABSTRACT

Generating a right-eye image by combining a right-side capturing image (4° capturing image) of a right breast with a left-side capturing image (0° capturing image) of a left breast rotated by 180° such that the chest walls of the breasts face to each other and a left-eye image by combining a left-side capturing image (0° capturing image) of the right breast with a right-side capturing image (4° capturing image) of the left breast rotated by 180° such that the chest walls of the breasts face to each other. Based on the right-eye and left-eye images generated in the manner described above, displaying a stereoscopic image on a monitor.

2 Claims, 3 Drawing Sheets

(51) Int. Cl.
*A61B 6/02* (2006.01)
*A61B 6/00* (2006.01)
*G02B 27/22* (2006.01)
*H04N 13/04* (2006.01)
*H04N 13/02* (2006.01)
*H04N 13/00* (2006.01)

(52) U.S. Cl.
CPC .................................... *G02B 27/22* (2013.01); *H04N 13/04* (2013.01); *A61B 6/466* (2013.01); *H04N 13/021* (2013.01); *H04N 13/0253* (2013.01); *H04N 13/004* (2013.01)
USPC .............................. 345/419; 382/128; 378/41

(56) References Cited

U.S. PATENT DOCUMENTS 6,760,469 B1 * 7/2004 Berestov et al. .............. 382/132
2007/0019848 A1 * 1/2007 Takeo .......................... 382/128
2011/0235776 A1 9/2011 Kusunoki

FOREIGN PATENT DOCUMENTS

| JP | 2010-110571 A | 5/2010 |
| JP | 2010-167129 A | 8/2010 |
| JP | 2010-268433 A | 11/2010 |
| JP | 2011-206206 A | 10/2011 |

OTHER PUBLICATIONS

Written Opinion of the International Searching Authority, mailed Aug. 14, 2012, issued in PCT/JP2012/002168.
Extended European Search Report issued in European Application No. 12763499.6 on Sep. 29, 2014.
Japanese Office Action issued in Japanese Patent Application No. 2013-507190 on Sep. 2, 2014.

* cited by examiner

US 8,963,917 B2

RADIOLOGICAL BREAST IMAGE DISPLAY METHOD, RADIOLOGICAL BREAST IMAGE DISPLAY APPARATUS, AND PROGRAM

CROSS REFERENCE TO RELATED APPLICATIONS

This application is a Continuation of PCT International Application No. PCT/JP2012/002168 filed on Mar. 29, 2012, which claims the benefit of U.S. Provisional Application No. 61/470,041 filed on Mar. 31, 2011. The entire contents of all of the above applications are hereby incorporated by reference.

TECHNICAL FIELD

The present invention relates to a radiological breast image display method, radiological breast image display apparatus, and program for generating, based on four images of a right-side capturing image and a left-side capturing image of each of left and right breasts captured so as to have a parallax in a left-right direction, two images of right-eye and left-eye images, each representing the left and right breasts in the same image, and displaying a stereoscopic image formed of these images on a display unit capable of displaying a stereoscopic image.

BACKGROUND ART

Heretofore, it is known that a stereovision can be obtained through the use of parallax by displaying two images of right-eye and left-eye images in combination. Such a stereoscopically viewable image (hereinafter, stereoscopic image or stereo image) is generated based on a plurality of images having a parallax obtained by imaging the same subject from different directions.

The generation of such stereoscopic images is performed not only in the fields of digital cameras and televisions but also in the field of radiological image capturing. That is, it is practiced that a plurality of radiological images having a parallax is obtained by applying radiation to a subject from different directions and detecting radiation transmitted through the subject with respect to each direction using a radiological image detector, and a stereoscopic image is generated based on these radiological images. The generation of the stereoscopic image in the manner described above allows a radiological image having a sense of depth to be observed, that is, it is possible to observe a radiological image more suitable for diagnosis as described, for example, Japanese Unexamined Patent Publication No. 2010-110571.

DISCLOSURE OF INVENTION

When generating a stereoscopic image with respect to radiological images of left and right breasts, two images having a parallax (0° capturing image and 4° capturing image) are captured for each of the left and right breasts, whereby four images are obtained as illustrated, for example, in FIG. 4.

When displaying a stereoscopic image of radiological breast images, a right-eye image is generated by combining the right-side capturing image (4° capturing image) of the right breast with the right side capturing image (4° capturing image) of the left breast rotate by 180° such that the chest walls of the breasts face to each other and a left-eye image is generated by combining the left-side capturing image (0° capturing image) of the right breast with the left-side capturing image (0° capturing image) of the left breast rotate by 180° such that the chest walls of the breasts face to each other as illustrated, for example, in FIG. 7. Then, the display of a stereoscopic image based on the right-eye and left-eye images generated in the manner described above allows a stereoscopic image representing the left and right breasts at the same time in the same image to be displayed, which is convenient for the observer as the stereoscopic image of the left and right breasts can be confirmed at a time.

When displaying a stereoscopic image representing the left and right breasts in the same image in the manner described above, the right-side capturing image and left-side capturing image of the left breast are rotated by 180° and combined. This causes front-back directions of the left and right breasts (jumping out/retracting directions in the stereoscopic image) to be reversed in the stereoscopic image, making the image very difficult to observe.

In view of the circumstances described above, it is an object of the present invention to provide a radiological breast image display method, radiological breast image display apparatus, and program capable of displaying, when displaying a stereoscopic image representing left and right breasts in the same image by combining chest walls of the left and right breasts so as to face to each other, the left and right breasts such that front-back directions of the breasts agree with each other in the stereoscopic image.

A radiological breast image display method of the present invention is a method for generating, based on four images of a right-side capturing image and a left-side capturing image of each of left and right breasts captured so as to have a parallax in a left-right direction, two images of right-eye and left-eye images, each representing the left and right breasts in the same image, and displaying a stereoscopic image formed of two images of the right-eye and left-eye images on a display unit capable of displaying the stereoscopic image, the method including the steps of:

providing one of the right-eye and left-eye images by combining one of the right-side capturing image and the left-side capturing image of the right breast with one of the right-side capturing image and the left-side capturing image of the left breast such that the chest walls of the breasts face to each other and the other of the right-eye and left-eye images by combining the other of the right-side capturing image and the left-side capturing image of the right breast with the other of the right-side capturing image and the left-side capturing image of the left breast such that the chest walls of the breasts face to each other, wherein the image combining is performed such that front-back directions of the left and right breasts agree with each other in the stereoscopic image; and displaying a stereoscopic image formed of two images of the right-eye and left-eye images on the display unit.

As for the method of generating the right-eye and left-eye images such that the front-back directions of the left and right breasts agree with each other in the stereoscopic image may include but not limited to a method in which one of the right-eye and left-eye images is provided by combining the right-side capturing image of one breast with the left-side capturing image of the other breast rotated by 180° among the left and right breast images such that the chest walls of the breasts face to each other and the other of the right-eye and left-eye images is provided by combining the left-side capturing image of the one breast with the right-side capturing image of the other breast rotated by 180° among the left and right breast images such that the chest walls of the breasts face to each other and a method in which one of the right-eye and left-eye images is provided by combining the right-side capturing image of one breast with the right-side capturing image of the other breast flipped upside down among the left and right breast images such that the chest walls of the breasts face to each other and the other of the right-eye and left-eye images is provided by combining the left-side capturing image of the one breast with the left-side capturing image of the other breast flipped upside down among the left and right breast images such that the chest walls of the breasts face to each other.

Further, the radiological breast image display method of the present invention may be provided as a program for causing a computer to perform the method.

A radiological breast image display apparatus of the present invention is an apparatus for generating, based on four images of a right-side capturing image and a left-side capturing image of each of left and right breasts captured so as to have a parallax in a left-right direction, two images of right-eye and left-eye images, each representing the left and right breasts in the same image, and displaying a stereoscopic image formed of two images of the right-eye and left-eye images on a display unit capable of displaying the stereoscopic image, the apparatus including:

an image combining unit for providing one of the right-eye and left-eye images by combining one of the right-side capturing image and the left-side capturing image of the right breast with one of the right-side capturing image and the left-side capturing image of the left breast such that the chest walls of the breasts face to each other and the other of the right-eye and left-eye images by combining the other of the right-side capturing image and the left-side capturing image of the right breast with the other of the right-side capturing image and the left-side capturing image of the left breast such that the chest walls of the breasts face to each other, wherein the image combining is performed such that front-back directions of the left and right breasts agree with each other in the stereoscopic image; and a display control unit for displaying a stereoscopic image formed of two images of the right-eye and left-eye images on the display unit.

Here, the image combining unit may be a unit that provides one of the right-eye and left-eye images by combining the right-side capturing image of one breast with the left-side capturing image of the other breast rotated by 180° among the left and right breast images such that the chest walls of the breasts face to each other and the other of the right-eye and left-eye images by combining the left-side capturing image of the one breast with the right-side capturing image of the other breast rotated by 180° among the left and right breast images such that the chest walls of the breasts face to each other or a unit that provides one of the right-eye and left-eye images by combining the right-side capturing image of one breast with the right-side capturing image of the other breast flipped upside down among the left and right breast images such that the chest walls of the breasts face to each other and the other of the right-eye and left-eye images by combining the left-side capturing image of the one breast with the left-side capturing image of the other breast flipped upside down among the left and right breast images such that the chest walls of the breasts face to each other.

According to the radiological breast image display method, radiological breast image display apparatus, and program of the present invention, right-eye and left-eye images are generated such that front-back directions of the left and right breasts agree with each other in a stereoscopic image. When displaying a stereoscopic image representing left and right breasts at the same time in the same image by combining the chest walls of the left and right breasts face to each other, this allows the left and right breasts to be displayed such that front-back directions of the breasts agree with each in the stereoscopic image.

Here, if one of the right-eye and left-eye images is provided by combining the right-side capturing image of one breast with the left-side capturing image of the other breast rotated by 180° among the left and right breast images such that the chest walls of the breasts face to each other and the other of the right-eye and left-eye images is provided by combining the left-side capturing image of the one breast with the right-side capturing image of the other breast rotated by 160° among the left and right breast images such that the chest walls of the breasts face to each other or one of the right-eye and left-eye images is provided by combining the right-side capturing image of one breast with the right-side capturing image of the other breast flipped upside down among the left and right breast images such that the chest walls of the breasts face to each other and the other of the right-eye and left-eye images is provided by combining the left-side capturing image of the one breast with the left-side capturing image of the other breast flipped upside down among the left and right breast images such that the chest walls of the breasts face to each other, the present invention may be realized in a simple way.

BEST MODE FOR CARRYING OUT THE INVENTION

Figure 1:
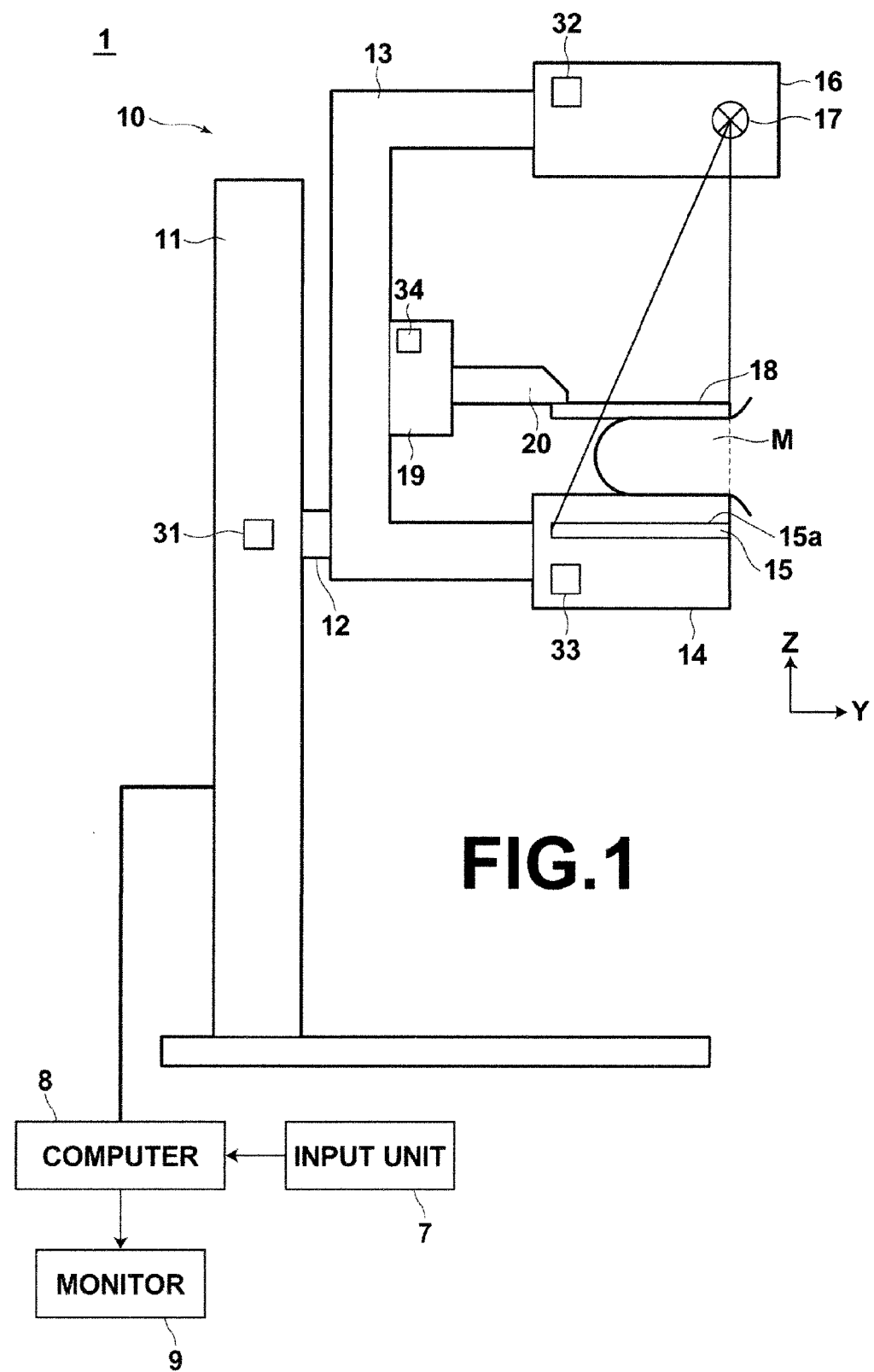
FIG. 1 is a schematic configuration diagram of a stereoscopic breast image capturing and display system that uses a radiological breast image display apparatus according to an embodiment of the present invention.
Figure 2:
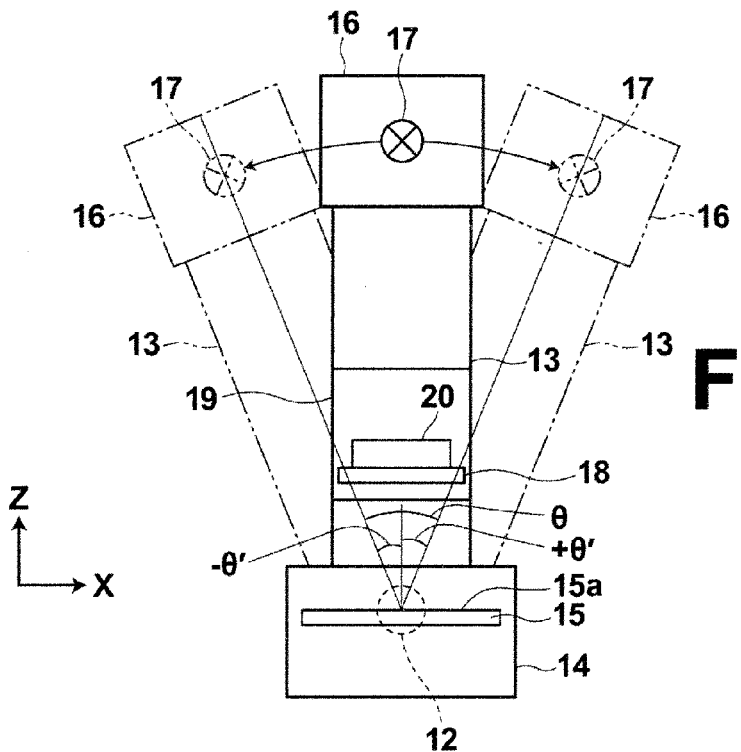
FIG. 2 illustrates the arm section of the stereoscopic breast image capturing and display system viewed from the right in FIG. 1.
Figure 3:
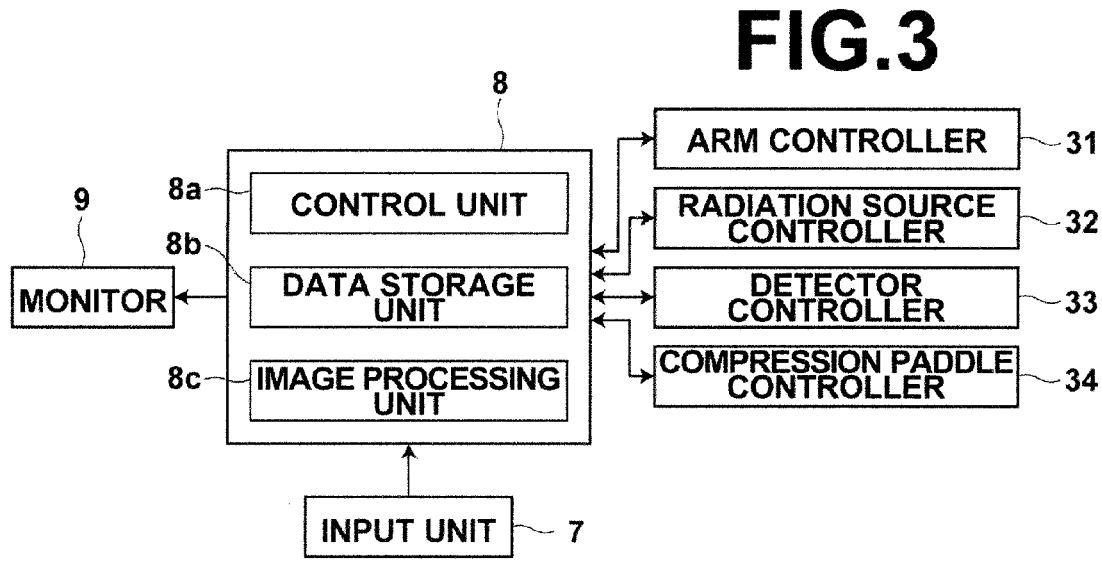
FIG. 3 is an internal block diagram of the computer of the stereoscopic breast image capturing and display system, illustrating a schematic configuration thereof.

Hereinafter, a stereoscopic breast image capturing and display system that uses a radiological breast image display apparatus according to an embodiment of the present invention will be described. A schematic configuration of the overall stereoscopic breast image capturing and display system will be described first. FIG. 1 is a schematic configuration diagram of the stereoscopic breast image capturing and display system that uses a radiological breast image display apparatus according to an embodiment of the present invention. FIG. 2 illustrates the arm section of the stereoscopic breast image capturing and display system viewed from the right in FIG. 1 and FIG. 3 is an internal block diagram of the computer of the stereoscopic breast image capturing and display system, illustrating a schematic configuration thereof.

The stereoscopic breast image capturing and display system 1 includes a breast image capturing apparatus 10, a computer 8 connected to the breast image capturing apparatus 10, and a monitor 9 (display unit) and an input unit 7 connected to the computer 8.

As illustrated in FIG. 1, the breast image capturing apparatus 10 includes a base 11, a rotary shaft 12 which is movable in up-down directions (Z directions) with respect to the base 11 and rotatable, and an arm section 13 coupled to the base 11 by the rotary shaft 12. FIG. 2 illustrates the arm section 13 viewed from the right in FIG. 1.

The arm section 13 has a shape of letter C with an imaging platform 14 at one end and a radiation application unit 16 at the other end attached so as to face the imaging platform 14. The movement of the arm section 13 in up and down directions is controlled by an arm controller 31 built in the based 11.

The imaging platform 14 includes, inside thereof, a radiological image detector 15, such as a flat panel detector or the like, and a detector controller 33 for controlling the reading of a charge signal from the radiological image detector 15 and the like. The imaging platform 14 further includes, inside thereof, a circuit board having thereon a charge amplifier for converting a charge signal read from the radiological image detector 15 to a voltage signal, a correlated double sampling circuit for sampling voltage signals outputted from the charge amplifier, an AD converter for converting the voltage signals to digital signals, and the like.

The imaging platform 14 is rotatably structured with respect to the arm section 13 and is fixedly oriented with respect to the base 11 even when the arm section 13 is rotated with respect to the base 11.

The radiological image detector 15 allows repeated use for recording and reading of radiation images, and a so-called direct type radiological image detector that generates a charge by directly receiving radiation or a so-called indirect type radiological image detector that converts radiation first to visible light and then converts the visible light to a charge signal may be used as the radiological image detector 15. As for the radiation image signal reading method, a so-called TFT (thin film transistor) reading method in which a radiation image signal is read by ON/OFF switching thin film transistors and a so-called optical reading method in which a radiation image signal is read by illuminating reading light are preferably used, but other method may also be used.

The radiation application unit 16 includes, inside thereof, a radiation source 17 and a radiation source controller 32. The radiation source controller 32 controls the emission timing of radiation from the radiation source 17 and the generation conditions of radiation (tube current, tube voltage, duration, and the like) in the radiation source 17.

Further, a compression paddle 18 disposed above the imaging platform 14 for holding and compressing a breast M, a support 20 for supporting the compression paddle 18, and a moving mechanism 19 for moving the support 20 in up-down directions (Z directions) are provided on a central portion of the arm section 13. The position and compression pressure of the compression paddle 18 are controlled by a compression paddle controller 34.

The computer 8 includes a central processing unit (CPU) and a storage device, such as a semiconductor memory, hard disk, SSD, or the like, and these pieces of hardware form a control unit 8a, a data storage unit 8b, and image processing unit 8c, as illustrated in FIG. 3.

The control unit 8a outputs a predetermined control signal to each of controllers 31 to 34 and performs control over the entire system, as well as functioning as a display control unit for displaying a stereoscopic image formed of two images of left-eye and right-eye images on the monitor 9. A specific control method will be described later in detail. The data storage unit 8b stores radiological image data with respect to each image capturing angle obtained by the radiological image detector 15. The image processing unit 8c performs various types of image processing as well as functioning as an image combining unit for generating, based on four images of a right-side capturing image and a left-side capturing image of each of left and right breasts captured so as to have a parallax in a left-right direction, two images of right-eye and left-eye images, each representing the left and right breasts in the same image. That is, the computer 8 functions also as the radiological breast image display apparatus.

The input unit 7 includes a pointing device, such as a keyboard, a mouse, or the like and receives input, such as an imaging condition, an operational instruction, and the like.

The monitor 9, as the display unit, is structured to use two radiological image (right-eye and left-eye image) signals outputted from the computer 8 and to display the two radiological images as two-dimensional images, thereby displaying a stereoscopic image in a stereoscopically viewable manner.

As for the arrangement for displaying a stereoscopic image, for example, an arrangement may be adopted in which two screens are used to display radiation images based on image signals of the two radiation images respectively, and one of the radiation images is inputted to the right eye of the observer while the other of which is inputted to the left eye of the observer using half mirrors or polarization glasses, thereby displaying a stereoscopic image.

Otherwise, for example, an arrangement may be adopted in which two radiation images are superimposed on top of each other and displayed by shifting a predetermined amount of parallax, and a stereoscopic image is generated by observing the superimposed images with polarization glasses. Still further, an arrangement may be adopted in which a stereoscopic image is generated by displaying two radiation images on a 3D liquid crystal capable of providing stereoscopic vision, as in the parallax barrier method or lenticular process.

Further, separate devices may be used for displaying the stereoscopic image and two-dimensional images or the same device may be used if it is capable of displaying them on the same screen.

An operation of the breast image capturing and display system of the present embodiment will now be described.

First, either of the left or right breast M is placed on the imaging platform 14 and the breast M is compressed at a predetermined pressure by the compression paddle 18.

Then, an instruction to start image capturing is inputted at the input unit 7 after various imaging conditions, including an angle between two different image capturing directions (hereinafter, referred to as the "convergence angle $\theta$" and a combination of image capturing angles $\theta'$ that form the convergence angle $\theta$ are inputted.

Figure 4:
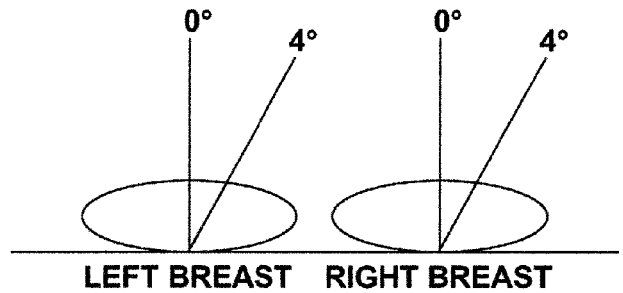
FIG. 4 illustrates image capturing of left and right breasts in the stereoscopic breast image capturing and display system described above.

When an instruction to start image capturing is given at the input unit 7, stereoscopic image capturing for the breast M is initiated. More specifically, the control unit 8a outputs information of convergence angle $\theta$ and image capturing angles $\theta'$ forming the angle of convergence 8 to the arm controller 31. In the present embodiment, it is assumed that $\theta=4°$ as the information of convergence angle $\theta$, and $\theta'=0°$ and $\theta'=4°$ as the combination of the image capturing angles forming the convergence angle $\theta$ are set, as illustrated in FIG. 4, but they are not limited to these and the radiographer may set any convergence angle $\theta$ at the input unit 7. Preferably, the convergence angle is set to a value in the range from 4° to 15° because too small or too large conversion angles make the stereovision difficult to obtain. As for the combination of image capturing angles θ', it is preferable that one of the image capturing angles θ', that is, the image capturing angle θ' for capturing an image for two-dimensional observation is 0°. This is because an image captured from the front of the radiological image detector 15 is most suited for two-dimensional observation.

The information of convergence angle θ outputted from the control unit 8a is received by the arm controller 31, which in turn outputs a control signal that causes the arm section 13 to be oriented perpendicular to the imaging platform 14 based on the information of convergence angle θ. That is, the arm controller 31 outputs a control signal that causes the image capturing angle θ' that makes the arm section 13 perpendicular to the detection surface 15a to be 0° in the present embodiment.

In response to the control signal outputted from the arm controller 31, the arm section 13 is rotated to the position of 0°. Then, the control unit 8a outputs control signals to the radiation source controller 32 and detector controller 33 to emit radiation and to read a radiological image signal respectively. In response to the control signals, radiation is emitted from the radiation source 17 and a radiological image of the breast M captured from the image capturing angle θ' of 0° is detected by the radiological image detector 15. Then, a radiological image signal is read by the detector controller 33 and stored in the data storage unit 8b of the computer 8.

Next, a control signal is outputted for causing the image capturing angle θ' that makes the arm section 13 inclined by 4° with respect to the direction perpendicular to the detection surface 15a.

In response to the control signal outputted from the arm controller 31, the arm section 13 is rotated to the position of 4°. Then, the control unit 8a outputs control signals to the radiation source controller 32 and detector controller 33 to emit radiation and to read a radiological image signal respectively. In response to the control signals, radiation is emitted from the radiation source 17 and a radiological image of the breast M captured from the image capturing angle θ' of 4° is detected by the radiological image detector 15. Then, a radiological image signal is read by the detector controller 33 and stored in the data storage unit 8b of the computer 8.

Subsequently, images of the other of the left and right breasts are captured in the same manner as described above and, as a result, four images of right-side capturing images (4° capturing images) and left-side capturing images (0° capturing images) captured so as to have a parallax in a left-right direction for each of the left and right breasts are obtained.

Next, an operation performed during a stereoscopic image is displayed will be described.

First, signals of four images of right-side images (4° capturing images) and left-side images (0° capturing images) of each of the left and right breasts are read from the data storage unit 8b of the computer 8 and sent to the image processing unit (image combining unit) 8c.

Figure 5:
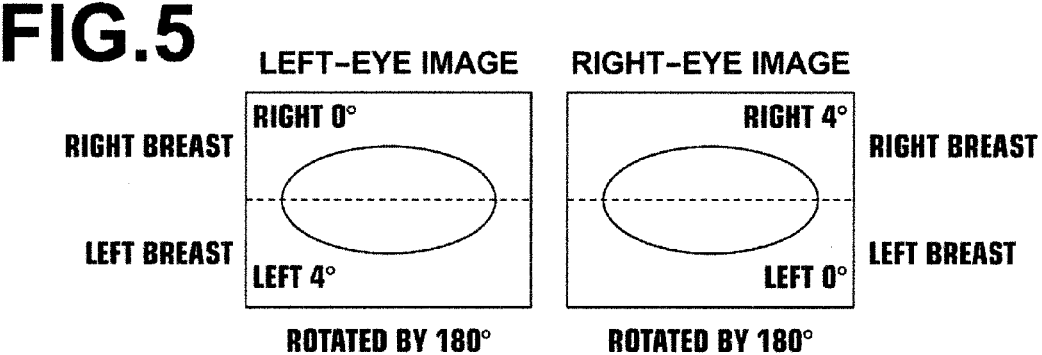
FIG. 5 illustrates an example of right-eye and left-eye images in the stereoscopic breast image capturing and display system described above.

In the image processing unit (image combining unit) 8c, a right-eye image is generated by combining the right-side capturing image (4° capturing image) of the right breast with the left-side capturing image (0° capturing image) of the left breast rotated by 180° such that the chest walls of the breasts face to each other and a left-eye image is generated by combining the left-side capturing image (0° capturing image) of the right breast with the right-side capturing image (4° capturing image) of the left breast rotated by 180° such that the chest walls of the breasts face to each other, as illustrated in FIG. 5.

Figure 6:
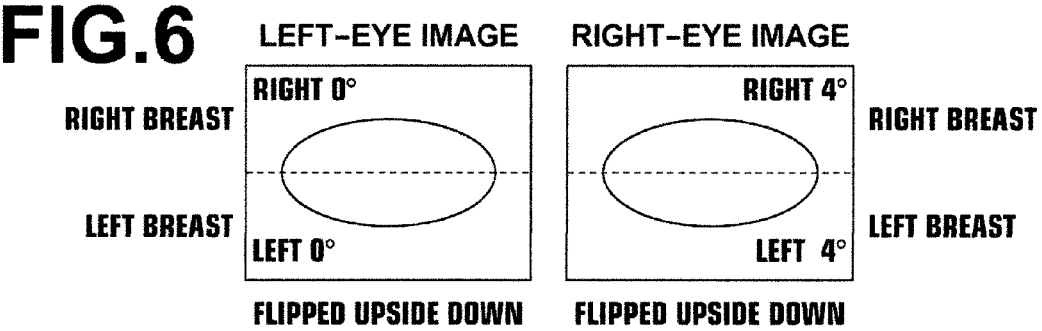
FIG. 6 illustrates another example of right-eye and left-eye images in the stereoscopic breast image capturing and display system described above.
Figure 7:
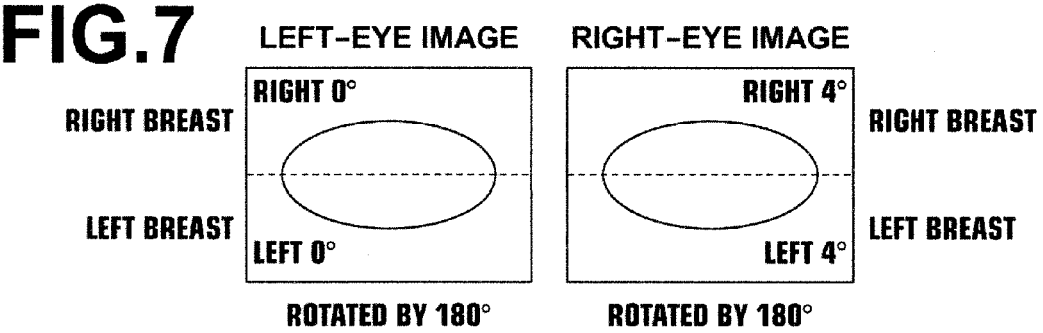
FIG. 7 illustrates an example of right-eye and left-eye images in a conventional stereoscopic breast image capturing and display system.

Note that the processing here is not limited to that described above, and a right-eye image may be generated by combining the right-side capturing image (4° capturing image) of the right breast with the right-side capturing image (4° capturing image) of the left breast flipped upside down such that the chest walls of the breasts face to each other and a left-eye image may be generated by combining the left-side image (0° capturing image) of the right breast with the left-side capturing image (0° capturing image) of the left breast flipped upside down such that the chest walls of the breasts face to each other, as illustrated in FIG. 6.

Two image signals of the right-eye image and left-eye image generated in the manner described above are outputted to the monitor 9 and a stereoscopic image representing the left and right breasts in the same screen is displayed on the monitor 9.

Such arrangement allows the left and right breasts to be displayed in a stereoscopic image in agreement with each other in front-back directions.

So far a preferred embodiment of the present invention has been described, but it should be understood that the present invention is not limited to the embodiment described above and various modifications and changes may be made without departing from the spirit and scope of the invention.

What is claimed is:

1. A radiological breast image display method for generating, based on four images of a right-side capturing image and a left-side capturing image of each of left and right breasts captured so as to have a parallax in a left-right direction, two images of right-eye and left-eye images, each representing the left and right breasts in the same image, and displaying a stereoscopic image formed of two images of the right-eye and left-eye images on a display unit capable of displaying the stereoscopic image, the method including the steps of:

providing one of the right-eye and left-eye images by combining one of the right-side capturing image and the left-side capturing image of the right breast with one of the right-side capturing image and the left-side capturing image of the left breast such that the chest walls of the breasts face to each other and the other of the right-eye and left-eye images by combining the other of the right-side capturing image and the left-side capturing image of the right breast with the other of the right-side capturing image and the left-side capturing image of the left breast such that the chest walls of the breasts face to each other, wherein the image combining is performed such that front-back directions of the left and right breasts agree with each other in the stereoscopic image, wherein:

one of the right-eye and left-eye images is provided by combining the right-side capturing image of one breast with the left-side capturing image of the other breast rotated by 180° among the left and right breast images such that the chest walls of the breasts face to each other, and the other of the right-eye and left-eye images is provided by combining the left-side capturing image of the one breast with the right-side capturing image of the other breast rotated by 180° among the left and right breast images such that the chest walls of the breasts face to each other, for matching the front to back directions of the right and left breasts; and displaying a stereoscopic image formed of two images of the right-eye and left-eye images on the display unit.

2. A radiological breast image display apparatus for generating, based on four images of a right-side capturing image and a left-side capturing image of each of left and right breasts captured so as to have a parallax in a left-right direction, two images of right-eye and left-eye images, each representing the left and right breasts in the same image, and displaying a stereoscopic image formed of two images of the right-eye and left-eye images on a display unit capable of displaying the stereoscopic image, the apparatus comprising:

an image combining unit for providing one of the right-eye and left-eye images by combining one of the right-side capturing image and the left-side capturing image of the right breast with one of the right-side capturing image and the left-side capturing image of the left breast such that the chest walls of the breasts face to each other and the other of the right-eye and left-eye images by combining the other of the right-side capturing image and the left-side capturing image of the right breast with the other of the right-side capturing image and the left-side capturing image of the left breast such that the chest walls of the breasts face to each other, wherein the image combining is performed such that front-back directions of the left and right breasts agree with each other in the stereoscopic image, wherein the image combining unit is a unit that provides
one of the right-eye and left-eye images by combining the right-side capturing image of one breast with the left-side capturing image of the other breast rotated by 180° among the left and right breast images such that the chest walls of the breasts face to each other and the other of the right-eye and left-eye images by combining the left-side capturing image of the one breast with the right-side capturing image of the other breast rotated by 180° among the left and right breast images such that the chest walls of the breasts face to each other for matching the front to back directions of the right and left breasts; and a display control unit for displaying a stereoscopic image formed of two images of the right-eye and left-eye images on the display unit.

* * * * *